United States Patent [19]

Raviv et al.

[11] Patent Number: 4,649,482
[45] Date of Patent: Mar. 10, 1987

[54] BRAIN ELECTRICAL ACTIVITY TOPOGRAPHICAL MAPPING

[75] Inventors: Gabriel Raviv, Des Plaines; Gil Raviv, Deerfield, both of Ill.

[73] Assignee: Bio-logic Systems Corp., Mundelein, Ill.

[21] Appl. No.: 646,613

[22] Filed: Aug. 31, 1984

[51] Int. Cl.$^4$ .......................... A61B 5/04; G06F 15/42
[52] U.S. Cl. ..................................... 364/417; 128/731
[58] Field of Search ....................... 364/413, 415, 417; 128/731

[56] References Cited

U.S. PATENT DOCUMENTS

| | | | |
|---|---|---|---|
| 3,901,215 | 8/1975 | John | 128/731 |
| 4,286,291 | 8/1981 | Taylor et al. | 358/138 |
| 4,354,243 | 10/1982 | Ryan et al. | 364/515 |
| 4,407,299 | 10/1983 | Culver | 128/731 |
| 4,408,616 | 10/1983 | Duffy et al. | 128/731 |
| 4,421,122 | 12/1983 | Duffy | 128/731 |
| 4,428,059 | 1/1984 | Gessert | 364/577 |
| 4,498,080 | 2/1985 | Culver | 128/731 X |
| 4,528,585 | 7/1985 | Bolger | 358/22 |
| 4,533,346 | 8/1985 | Cosgrove, Jr. et al. | 123/731 X |

OTHER PUBLICATIONS

Buchsbaum, M. S. et al. "A New System for Gray-Level Surface Distribution Maps of Electrical Activity", *Electroencephalography and Neurophysiology*, vol. 53, No. 2, Feb. 1982, 237–242.

Duffy, F. H. "Topographic Display of Evoked Potentials: Clinical Applications of Brain Electrical Activity Mapping (BEAM)", *Annals New York Academy of Sciences*, vol. 388, 1982, 183–196.

Buchsbaum, M. S. et al. "New Methods to Determine the CNS Effects of Antigeriatric Compounds: EEG Topography and Glucose Use", *Drug Development Research*, vol. 2, No. 5, 1982, 489–496.

Sandini, G. et al. "Topography of Brain Electrical Activity: a Bioengineering Approach", *Medical Progress through Technology*, vol. 10, No. 1, 1983, 5–18.

Walter, D. O. et al. "Computerized Topo-EEG Spectral Maps; Difficulties and Perspectives", *Neuropsychobiology*, vol. 11, No. 4, 1984, 264–272.

Ashida, H. et al. "Field Mapping of EEG by Unbiased Polynomial Interpolation", *Computers and Biomedical Research*, vol. 17, No. 3, Jun. 1984, 267–276.

Buchsbaum, M. E. et al. "Topographic Cortical Mapping of EEG Sleep Stages During Daytime Naps in Normal Subjects", *Sleep*, vol. 5, No. 3, 1982, 248–255.

*Primary Examiner*—Jerry Smith
*Assistant Examiner*—Clark A. Jablon
*Attorney, Agent, or Firm*—Niro, Scavone, Haller & Niro, Ltd.

[57] ABSTRACT

An apparatus for monitoring and operating on brain input activity signals to provide topographical maps characteristic of patient brain activity. The apparatus senses the brain input activity signals and processes the signals to provide detailed information on patient brain activity. Complete topographical maps of the patient brain are activity constructed by a line-by-line interpolation method. A color coded scale adjacent the topographical map is utilized to provide additional information on patient brain activity. The user has a number of options available to select various information for display and analysis.

28 Claims, 9 Drawing Figures

SIGNAL = MEMORY I + MEMORY II + NOISE
NOISE = MEMORY I − MEMORY II

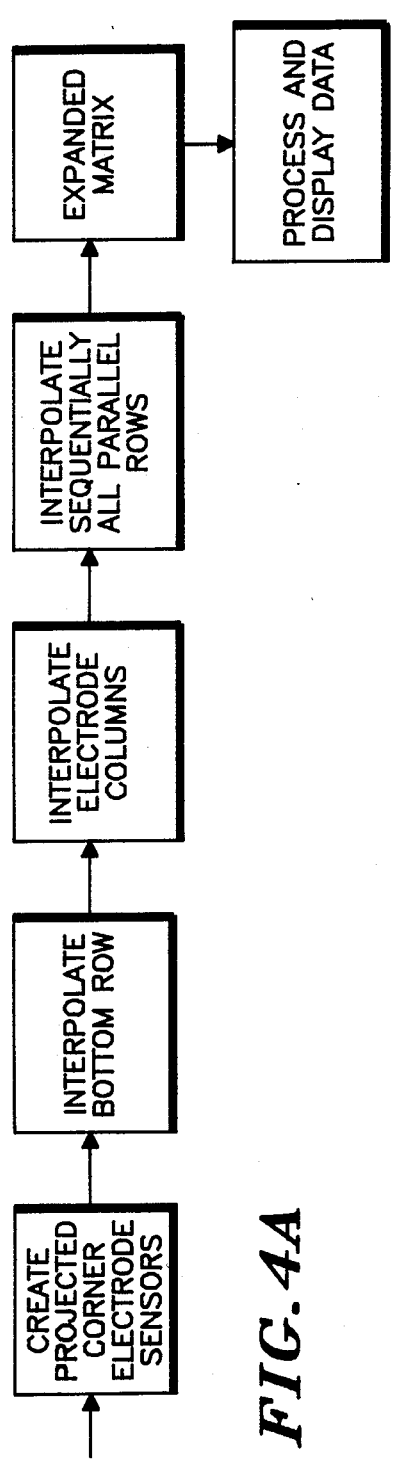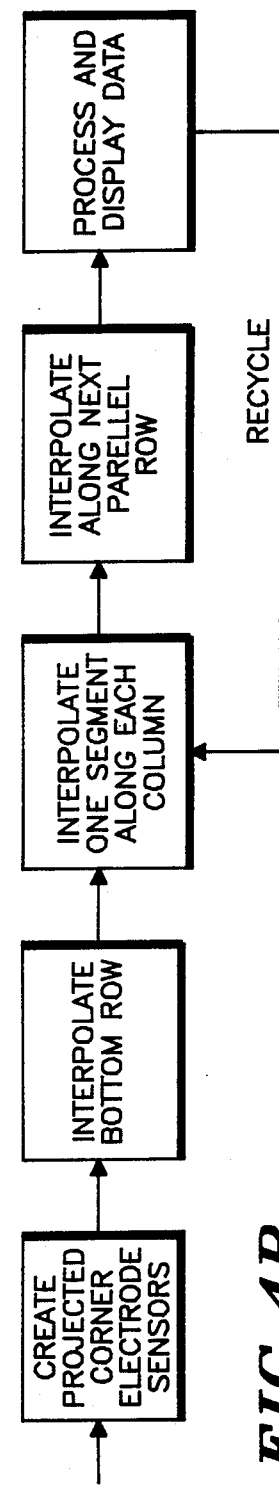
FIG. 4A
FIG. 4B

BRAIN ELECTRICAL ACTIVITY TOPOGRAPHICAL MAPPING

The present invention relates generally to an apparatus and method for displaying a topographical map of brain electrical activity of a patient, and more particularly to a novel method and apparatus for performing rapid manipulation of data using computer software to provide line-by-line interpolation of input activity signals and output of a plurality of topographical maps having a variety of information characteristic of brain electrical activity.

Information on brain electrical activity is typically obtained by performing evoked potential (EP) response measurements and electroencephelogram (EEG) measurements. Such measurements often yield a set of complicated time varying outputs. A detailed and thorough analysis of these complicated outputs requires computer manipulation to determine differences of brain electrical activity of a selected patient compared to a representative normal population. A number of limitations currently exist for computer manipulation and analysis of these brain electrical activity measurements. In prior computerized apparatus the brain electrical activity measurements have been performed using a large number of system components to carry out the tasks of measurement, analysis and display of data. Consequently, such computerized systems are costly to purchase and maintain, and the system is unnecessarily complicated. Furthermore, prior computerized systems for measurement and output of brain electrical activity generate the topographical maps without clearly associating all the appropriate data and without manipulating and displaying the optimum available data combinations. For examples of various prior approaches, see, U.S. Pat. Nos. 4,408,616; 4,417,591; 4,201,224 and 4,421,122; which are incorporated by reference herein. Therefore, in order to obtain the maximum benefit and understanding from the measured brain electrical activity, it is essential to manipulate, use and display the data to the viewer in the best manner possible.

BREIF SUMMARY OF THE INVENTION

One of the primary objects of the invention is to provide an improved apparatus and method for displaying a topographical map of brain electrical activity.

A more particular object of the invention is to provide a novel apparatus and a method for manipulating brain electrical activity signals using computer software to provide a video display of topographical maps of brain electrical activity.

Another object of the invention is to provide a novel method and apparatus for generating a video display of brain electrical activity signals interpolated and output for display on a line-by-line basis for positions between, as well as at, the electrode sensors on a patient's head.

An additional object of the invention is to provide an improved method and apparatus for displaying a topographical map of brain electrical activity signals and including in the display a fixed color code scale wherein each color in the topographical map has a relative value determined by correlation with each color in the fixed color scale.

Another object of the invention is to provide a method and apparatus for simultaneously displaying a plurality of topographical maps of different selectable states of brain electrical activity signals.

A further object of the invention is to provide an improved method and apparatus for increasing the rate of display of topographical maps of brain electrical activity signals by interlacing the output to the display memory of every other pixel line in each of the topographical maps of brain electrical activity.

In accordance with the invention an apparatus and method for measuring and displaying topographical maps of brain electrical activity uses computer software to generate interpolated outputs of the brain electrical activity signals and to carry out additional analysis and then output the results to a display processing unit. A user can select for display a plurality of the topographical maps which illustrate various characteristics of brain electrical activity signals, such as evoked potential (EP) response information and electroencephelogram (EEG) information. The brain electrical activity is measured by electrode sensors which generate input activity signals. These input activity signals are interpolated line-by-line to generate an expanded finer matrix of interpolated values. Interpolation is selectively performed every other pixel line in the interlace mode of constructing the topographical map. The display of characteristic data includes a color code scale and associated numerical values for determining the relative magnitudes of regions of the topographical map. In addition to the topographical maps, individual characteristic waveforms and other associated parameters can be simultaneously output to a video display or printer for comparison and association with the topographical maps.

Further objects and advantages of the present invention, together with the organization and manner of operation thereof, will become apparent from the following detailed description of the invention when taken in conjunction with the accompanying drawings wherein like reference numerals designate like elements throughout the several views.

BRIEF DESCRIPTION OF THE DRAWINGS

FIGS. 4A and 4B are block diagrams of two alternative methods for line-by-line interpolation and output of signals;

DESCRIPTION OF PREFERRED EMBODIMENTS

Figure 1A:
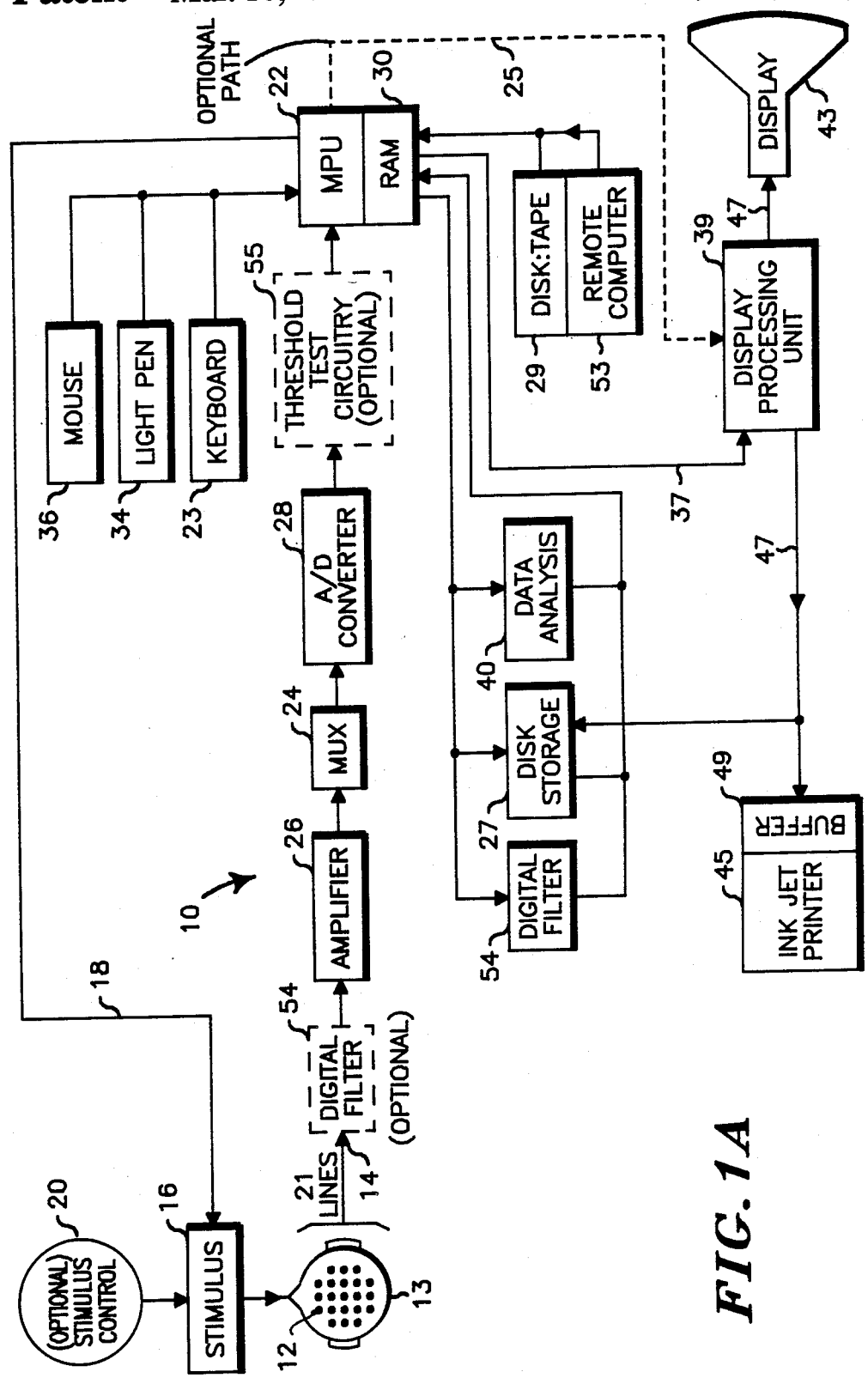
FIG. 1A is a block diagram of an apparatus for measuring brain electrical activity signals and for displaying topographic maps characteristic thereof, and FIGS. 1BA, 1BB is a functional block diagram showing the flow through the apparatus of the measured input activity signals.
Figure 2:
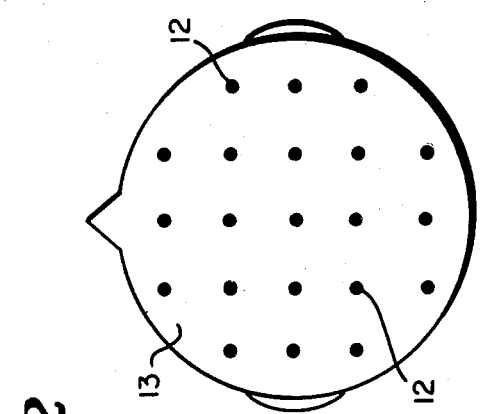
FIG. 2 shows a top view of positions of an electrode sensor arrangement with respect to a patient head outline.

Referring now to the drawings, and in particular to FIG. 1A, a block diagram of a brain electrical activity mapping apparatus constructed in accordance with one embodiment of the present invention is indicated generally at 10. The brain electrical activity mapping apparatus (hereinafter referred to as the apparatus 10) includes sensor means, such as, for example, a set of electrode sensors 12 (for example, Grass gold cup manufactured by Grass Corporation) arranged on the top of a patient's head 13. In FIG. 2 is shown an enlarged detail of a preferred arrangement for a rectangular array or matrix of twenty-one of the electrode sensors 12 positioned on the patient's head 13. The arrangement illustrates one acceptable variety selected from various conventional international formats. In response to brain electrical activity the electrode sensors 12 generate input activity signals 14.

In selected operating modes of the apparatus 10, such as in measurement of evoked potential (hereinafter "EP") response, a stimulus 16 is also applied to the patient, and in response to the stimulus 16 the resulting brain electrical activity is sensed by the electrode sensors 12. A detailed discussion of EP response measurements is set forth in Duffy et al., "Brain Electrical Activity Mapping (BEAM): A Method for Extending the Clinical Utility of EEG and Evoked Potential Data," Annals of Neurology 5, Apr., 1979, pp. 209–231; which is incorporated by reference herein. The type of stimulus 16 used in EP response measurements is, for example, a strobe light, a sound (such as a click generator) or a somatosensory stimulus, such as mild electrical shock. These stimuli 16 can be periodic, aperiodic and can also be combinations of each available type of the stimulus 16. In the illustrated embodiment of FIG. 1A, the stimulus 16 is controlled responsive to a control signal 18 from a main computer, such as a microprocessor unit 22. The type of stimulus 16 is selected by a user input, such as a keyboard 23. In alternative forms of the invention, the stimulus 16 is provided responsive to a stimulus controller 20 which is a separate microcomputer or is a remote control source.

In other modes of operation of the apparatus 10, such as in electroencephelogram (hereinafter "EEG") measurements, the stimulus 16 is not applied to the patient. However, the measurement of brain electrical activity in the EEG mode otherwise follows substantially the same steps as for EP measurement. Therefore, in general as shown in FIG. 1A, the sensed input activity signal 14 is output from the electrode sensors 12 to processing means which includes an analog multiplexer 24, an amplifier 26 and an analog to digital converter (A/D) 28. If a Grass or Beckman polygraph is used, the electrode sensors 12, the multiplexer 24 and the amplifier 26 are included in the polygraph.

In the illustrated embodiment the amplifier 26 comprises a plurality of twenty-one amplifiers, each connected to an associated one of the electrode sensors 12. The multiplexer 24 accepts from the amplifier 26 each of the amplified input activity signals 14, and outputs each of these input activity signals 14 in serial fashion to the A/D converter 28 (for example, a Dual Systems AIM 12). The A/D converter 28 provides to the microprocessor unit 22 an amplified and digitized, or a converted, form of the input activity signal 14. In general, processing means includes those components of the apparatus 10 which operate on the signals output by the electrode sensors 12 to provide the amplified and digitized form of the input activity signals 14.

The microprocessor unit 22 in FIG. 1A can be any one of a plurality of commercially available computers, such as, for example, a Zenith Z-100, which uses an 8088 central processor chip (see, Intel Component Data Catalog, January 1982, pp. 8–25 to 8–51, which is incorporated by reference herein). The Zenith Z-100 also includes the keyboard 23, a display processing unit (hereinafter "DPU") 39 which will be described in detail hereinafter, a disk drive (not shown) and on board random access memory (hereinafter "RAM") 30, and PROM and ROM (not shown) memories. The microprocessor unit 22 controls collection, manipulation and output of the input activity signals 14. In a preferred embodiment, the microprocessor unit 22 includes the RAM 30 which functions in part as an averaging means for storing at predetermined locations a running accumulation of the plurality of input activity signals 14. The microprocessor unit 22 adds each new incoming value for the signals 14 to the previous value and stores the total in the RAM 30 at the predetermined locations. This accumulation of the amplified and converted input activity signals 14 results in statistical averaging of the input activity signals 14 which improves the signal to noise ratio. Under typical operating conditions one to ten minutes of data averaging is desirable to obtain statistically meaningful values for the input activity signals 14.

In a preferred embodiment of the invention, the apparatus 10 controls data gathering and analysis responsive to software programs stored on a disk or tape 29, and the programs are read into the RAM 30 and executed by the microprocessor unit 22. The user interacts with the microprocessor unit 22 through input means to supply an input signal responsive to a user input. Examples of input means include the keyboard 23, a light pen 34 and a mouse 36. The user can also supply an input signal by transfer of information already stored on a disk storage unit 27 or stored in the disk or tape 29, or stored in a memory external to the apparatus 10, such as, for example, a remote computer memory (not shown). These various input means enable setting of variables such as the time period of data taking, the number and type of the stimuli 16 and the desired software programs to manipulate the data for output and display for user analyzation.

Figure 1B:
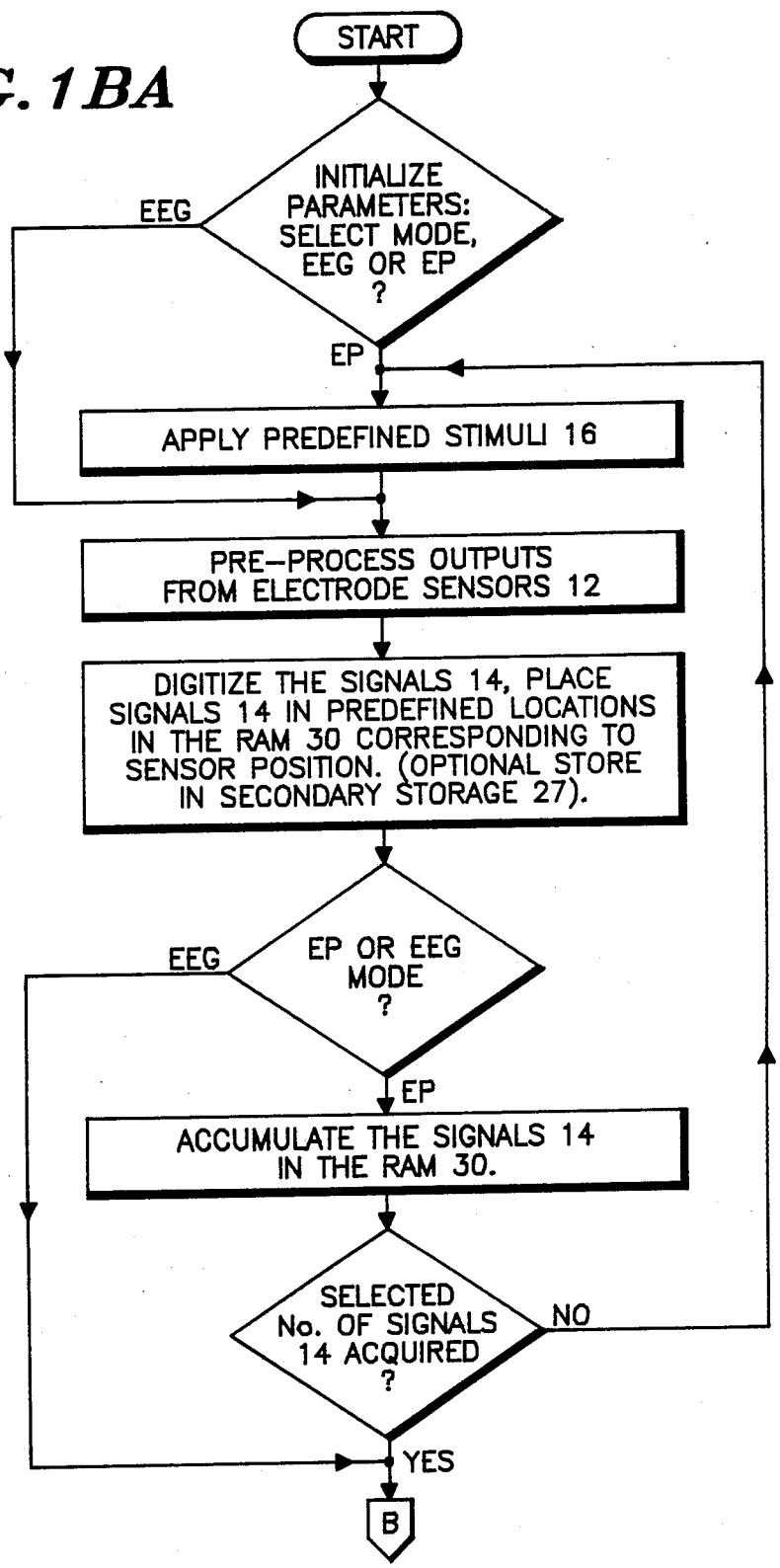

The operation of the apparatus 10 as illustrated in FIG. 1A can be better understood by reference to the procedural and signal flow diagram of FIG. 1BA and 1BB. As illustrated in FIG. 1BA, the apparatus 10 in the first decisional block has been initialized with user selected parameters or default parameters, and a mode of operation is selected. If the EP response mode is selected, then a predefined stimuli 16 is applied to the patient as a first step. However, if the EEG mode is selected, then there is no externally applied predefined stimuli 16, and the electrode sensors 12 detect EEG signals directly from the patient's head 13. In any event, whether the signals originate from the patient as an EEG signal or as an EP response signal, the next step is directed to preprocessing the outputs from the electrode sensors 12. This preprocessing can include, for example, a number of steps, including amplification, hardware filtering, software filtering and fast Fourier transformation.

The preprocessed outputs from the electrode sensors 12 are then digitized, and the digitized form of the signals 14 are placed in predefined locations in the RAM 30 corresponding to predefined sensor positions. The signals 14 corresponding to particular sensor positions can alternatively or additionally be stored in secondary storage, such as the disk storage unit 27 or the tape 29.

Once the signals 14 have been digitized and stored in the RAM 30, a determination is made whether the apparatus 10 is in the EEG or the EP mode. If operating in the EEG mode the procedure skips to step B shown in FIG. 1BB. If, however, the apparatus 10 is in the EP mode, the signals 14 are accumulated in the predefined locations in the RAM 30 and/or can be stored in the disk storage unit 27 or the tape 29. Operation of the apparatus 10 then proceeds to determine whether the selected number of signals 14 have been acquired in accordance with the initial setup parameters. If the selected number of the signals 14 has been acquired in the appropriate manner, processing proceeds to step B which continues in FIG. 1BB. If, however, the selected number of the signals 14 has not been acquired, then processing resumes at the step of applying the predefined stimuli 16. This operation of the apparatus 10 in the EP mode shown in FIG. 1BA continues until the selected number of the signals 14 have been acquired.

Referring to FIG. 1BB, the operation continues at step B from FIG. 1BA. At this point the RAM 30 contains data representative of the accumulation of the digitized signals 14 at predefined locations in the RAM 30 corresponding to respective sensor positions. Alternatively at this point, accumulated data signals can be input from a secondary storage source, such as the disk storage unit 27, to the RAM 30 to provide the initial database from which further manipulation proceeds. The next step in the operation is the selection of one of a plurality of options as to how to operate on the signals 14. Once the option is selected, the apparatus 10 proceeds to perform the appropriate operations on the signals 14 as stored and accumulated in the RAM 30. These operations on the signals 14 can include, for example, attenuation or amplification, digital filtering, smoothing, fast Fourier transformation, differentiation, integration and statistical data analysis. In other forms of the invention these operations can be performed prior to storage in the RAM 30, such as after the A/D conversion 28 and prior to initial storage in the RAM 30.

After the selected option has been performed, the result of the operation is stored again in the RAM 30, either at new locations or at the previous locations, such as by overwriting the previous locations with the new form of the signals 14. Alternatively or additionally, the results can be stored in a secondary storage such as the disk storage unit 27. At this point, the signals 14 stored in the RAM 30 provide the basis for interpolation, either line by line or in an interlaced or alternate line mode of output, and the interpolated form of the signals 14 is output in a display format compatible with the DPU 39. The DPU 39 therefore receives and stores the interpolated form of the signals 14 in the display RAM of the DPU 39, one line at a time, as shown in the next block of FIG. 1BB. The DPU 39 generates an image on a display means, such as a video display 43 (for example, a Zenith ZVM-133), or the image is output to another form of the display means, such as an ink jet printer 45 (for example, a TRS 80 CGP220 manufactured by Tandy Corp.).

Interpolation

In the illustrated form of the invention, the input activity signals 14 stored in the RAM 30 undergo an interpolation within the RAM 30 under control of the microprocessor unit 22. An expanded matrix is formed of finer resolution (for example, a forty by forty array of points in the preferred embodiment) than the arrangement of the twenty-one electrode sensors 12. The general technique of interpolation using three points to form finer resolution frames of the input activity signals 14 is known (see, for example, Duffy et al., "Brain Electrical Activity Mapping" referred to hereinbefore). However, as will be discussed hereinafter, the present invention includes an improved interpolation method which uses a set of two points to generate and output line-by-line the interpolated form of the input activity signals 14.

In the preferred embodiment, a line is one line of pixels, wherein a pixel is the smallest picture element used to construct the video image. As will be described in more detail hereinafter, each pixel color is described completely by three bits of digital information stored in the RAM 30. In alternative forms of the invention a color mapping procedure can be used to assign color values to the pixels. For example, each pixel can have five bits in the RAM 30 to describe one of thirty-two possible color choices which points to a color map also located in the RAM 30. The color map can have a preselected number of n bits of information which describes each of $2^n$ possible colors, and the color map digital description is output to the intensity digital to analog converter part of the DPU 39 for display of the desired pixel color.

Upon completion of the interpolation for a given line, the interpolated values can also be stored in a disk storage unit 27 for future use and analysis. A video output 37 of the interpolated input activity signals 14 is output line-by-line to the DPU 39 (preferably contained within the microprocessor unit 22 as discussed hereinbefore) in preparation for output to the video display 43. The interpolated form of the signals 14 can also be output from the RAM 30 or the DPU 39 for hard copy printout on the printer 45 or for completion of an additional data analysis 40 before being displayed. These alternative operations will be discussed in more detail hereinafter.

Figure 3:
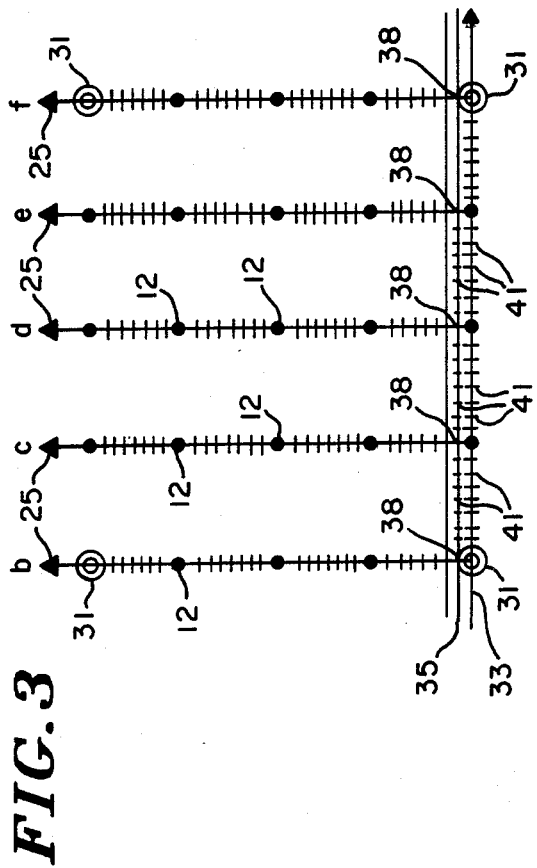
FIG. 3 is an array of electrode sensors and a superimposed image of a line-by-line interpolation of signals for the array.

In the illustrated embodiments of FIG. 3 and FIGS. 4A and 4B, the interpolation begins by generating amplitudes at four projected electrode sensors 31 at the corners of the matrix of the electrode sensors 12 to establish a rectangularly symmetric five by five matrix of the input activity signals 14. The values for the four signals 14 at the projected electrode sensors 31 are interpolated from a linear average projection from the intersecting perpendicular lines of the electrode sensors 12 which converge on each of the projected electrode sensors 31. Once the signals 14 have been established at each of the projected electrode sensors 31, the interpolation proceeds by selecting a first line, such as a line 33 in FIG. 3 along the perimeter of the matrix of the electrode sensors 12, and starting with line 33 the line-by-line interpolation is carried out parallel to the line 33.

The use of a commercial polygraph unit with, for example, twenty-one of the electrode sensors 12, rather than twenty-five actual sensors for the five by five matrix, enables use of a standard unit of substantially lower cost to the user. Further, the approximately rectangular arrangement for the twenty-one electrode sensors 12 enables the interpolation procedure to be simplified. In one form of the invention described in FIG. 4B interpolation proceeds along lines which are parallel to one another and pass through the regular array of points defined by the rectangular arrangement of the electrode sensors 12. Therefore, the interpolation takes place along one-dimensional lines which are easily defined in the rectangular arrangement and interpolation calculations are performed more easily using only two points to generate a bracketed intermediate point. In prior conventional interpolation approaches, three points from a nonrectangular arrangement have been used (see, for example, U.S. Pat. No. 4,417,591, which is incorporated by reference herein).

In a preferred form of the invention described in FIG. 4A, after determination of the signals 14 at the projected electrode sensors 31, the linear interpolation is carried out for selected points a predetermined fraction of the distance between each nearest neighbor pair of the signals 14 in a column 25 of the electrode sensors 12. An interpolated value for the selected point is determined by forming a linear weighted average of an appropriate pair of the input activity signals 14. This pair is either two of the signals 14 selected from the electrode sensors 12, or is one of the signals 14 at one of the electrode sensors 12 and one of the projected sensors 31, which bracket the location of the selected point. For example, in the illustrated embodiment of FIG. 3 the distance between each of the electrode sensors 12 is divided into eight parts. Thus, if the selected point is one-eighth of the distance between a first one of the sensors 12 and a second one of the sensors 12, then the value for the electrical activity signal 14 at the interpolated point is seven-eighths the value of the signal 14 at the first sensor 12 plus one-eighth the value of the signal 14 at the second sensor 12. This interpolation procedure continues sequentially up each of the columns 25 of the electrode sensors 12 until the interpolation is complete for all five of the columns 25 which are perpendicular to the line 33. The interpolation is then performed for all remaining lines parallel to the line 33, proceeding incrementally from line 33 to line 35 and to the other lines until completion.

In another form of the invention shown in FIG. 4B, after the interpolation along the line 33 has been completed, the interpolation proceeds point by point for the line 35 and for each of the subsequent lines parallel to the line 33. This procedure is accomplished by first determining the signal 14 at the selected point which is a predetermined fraction of the distance between the electrode sensor 12 contained in the line 33 and the nearest electrode sensor 12 in the same column 25. This process is completed for only a first point in each of the five columns 25 of the electrode sensors 12. The resulting five points are shown in FIG. 3 as interpolated values 38 which lie at the intersections of the columns 25 and the line 35. These values 38 are then used to complete the interpolation along the line 35 in the same manner as described above for the embodiment of FIG. 4A. Interpolated values 41 are therefore constructed from a linear weighted combination of the appropriate pair of the interpolated values 38 which bracket each of the values 41. The line 35 is then output for presentation on the video display 43. The outputted form of the signals 14 comprising the line 35 are therefore generated in a compatible format for the conventional video display 43. Further details of operation of the video display 43 can be obtained by reference to the Zenith ZVM-133 operating manual, which is incorporated by reference herein. Alternatively, the line 35 is output for the additional data analysis 40 prior to display, depending on the user selected operational mode. Display of the complete frame of a topographical map 44 shown in FIGS. 5 and 7 continues line-by-line, incrementally completing the interpolation for each of a plurality of lines and outputting each of the lines to the video display 43.

These interpolation procedures enable the live time line-by-line processing of the input activity signals 14 for output to the video display 43. The live time output and display of the signals 14 is accomplished without having to await formation of the entire video frame and also without having to store in the RAM 30 a plurality of the lines or a complete frame of the input activity signals 14 before output to the video display 43. Prior "live time"0 methods have required storage of the complete frame before the topographical map 44 could be displayed (see, for example, U.S. Pat. No. 4,417,591, which is incorporated by reference herein). Further, as mentioned hereinbefore, the present line-by-line interpolation requires only two end points to perform the procedure, and this greatly simplifies the calculation and storage of values in the RAM 30 and decreases the calculation and display time.

In some forms of the invention, the input activity signals 14 undergo other operations prior to the data interpolation, such as the data analysis 40 (for example, data smoothing and a digital filtering treatment to be discussed in more detail hereinafter). Another example of the data analysis 40 is the performance of a Fourier transformation of the EEG form of the input activity signals 14 from the twenty-one electrode sensors 12. In order to avoid performing time consuming Fourier transformation for the larger number of values in the expanded frame containing the interpolated values 38 and 41, only the small numbers (twenty-one in the illustrated embodiment) of the unexpanded input activity signals 14 undergo Fourier transformation. Interpolation expansion to a finer matrix is generally done more efficiently on the data after completion of any extensive or complicated form of signal treatment, such as the Fourier transformation operation.

Video Display

In the preferred embodiment, after the interpolation and the optional data analysis 40 of the input activity signals 14, the resulting video output 37 is applied to the DPU 39 contained in the Zenith Z-100 unit Alternatively, the raw input activity signals 14 accumulated in the RAM 30 can be output as a raw signal 25 by the microprocessor unit 22 to the DPU 39 without further processing, including interpolation. The video output 37 input to the DPU 39 is converted into an output signal 47 suitable for the video display 43 which provides the topographical map 44.

In the preferred embodiment there is one display rate, other than manually sequencing through the set of frames, for dynamic display of the change in EP response as a function of time elapsed after the stimulus 16 has been applied to the patient's head 13. The display rate can also be increased by generating reduced sizes of the topographical maps 44, in a manner to be described in detail hereinafter. Operation of a typical form of the DPU 39 has been discussed hereinbefore in the *Interpolation* section and is also explained in, "Fundamentals of Computer Graphics," J. D. Foley and A. Van Dam, Addison-Wesley Co., Reading, Mass., 1982, pp. 112–136, which is incorporated by reference herein. Also, see U.S. Pat. Nos. 4,121,283, 4,139,838 and 4,213,189 which are incorporated by reference herein.

In addition to the generation of the video display 43, as mentioned hereinbefore the interpolated input activity signals 14 are selectively stored in the disk storage unit 27 or applied to the ink jet printer 45 which provides a hard copy printout of the topographical map 44. The user selects print out of the topographical map 44 on the video display 43 by actuating transfer of the video output 47 to a page buffer 49 coupled to the ink jet printer 45. Upon filling the page buffer 49, the printer 45 outputs the hard copy printout.

Figure 5:
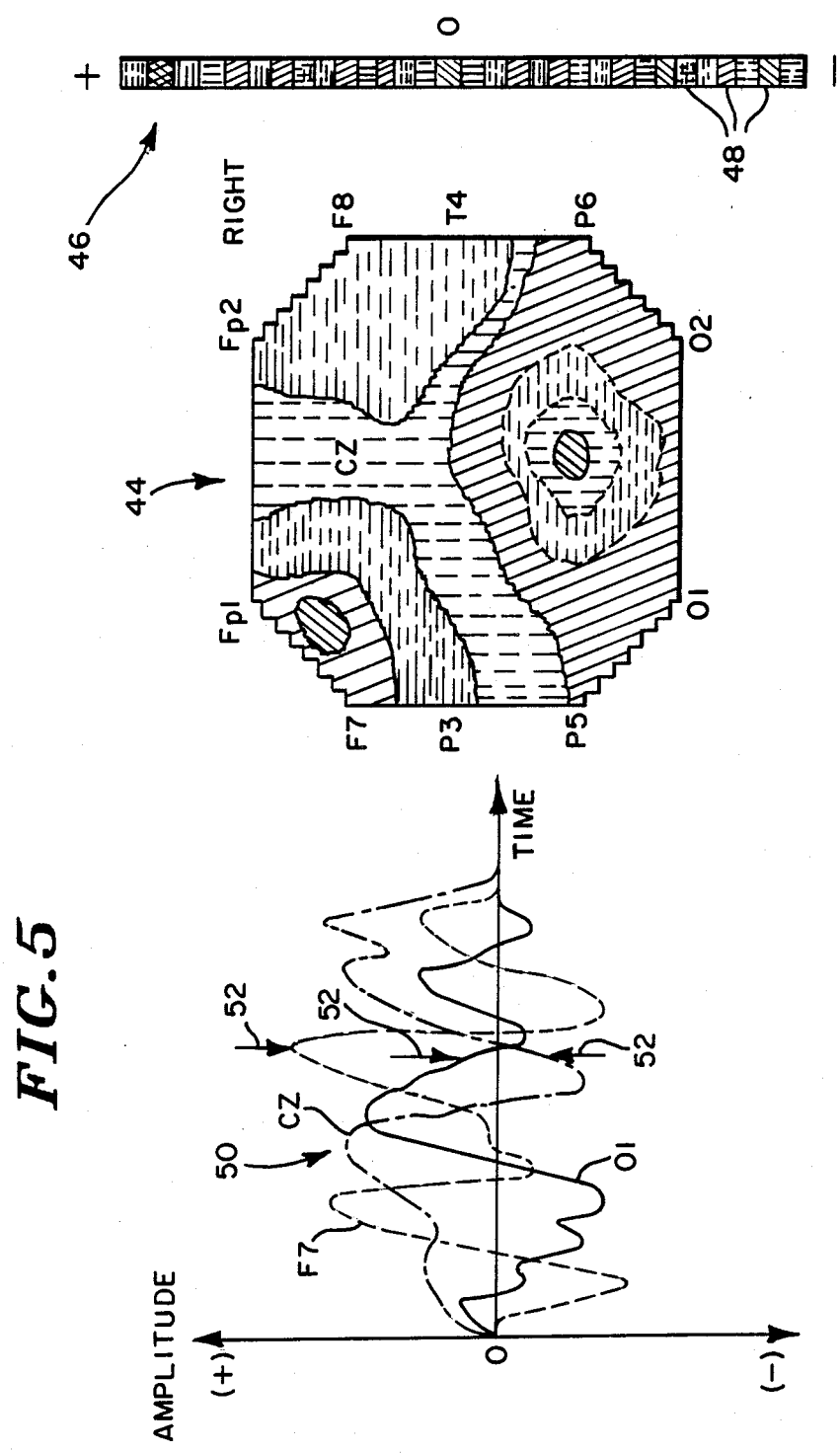
FIG. 5 is a display output of evoked potential (EP) response measurements showing a topographical map, associated waveforms for selected electrode sensor locations and a vertically positioned color code scale.

In the illustrated embodiment of FIG. 5, the topographical map 44 is color coded, and in a preferred form of the invention thirty-two different color choices are used to encode the relative magnitude of the brain electrical activity for the input activity signals 14 displayed on the topographical map 44. In the illustrated embodiment of FIGS. 1 and 5, color code means for encoding the colors on the topographical map 44 is accomplished in conjunction with a software program which is read into the RAM 30 from the disk 29. The topographical map 44 is constructed of blocks of two by four, or eight, pixels; and as mentioned hereinbefore each of the pixels in the block are described by three separate storage bits, one for each of the memory locations in the RAM 30 associated with the red, green and blue colors which are used to construct all the colors. With three storage bits per pixel a total of two cubed, or eight, unique colors can be constructed. These eight colors, along with white, are assigned to individual pixels in the block and are mixed to generate twenty-four more colors. For example, the block of two by four pixels can be constructed in a predetermined manner using the unique colors to arrange the colors of near neighbor pixels around a selected given pixel to form a block having a light yellow appearance. This is accomplished by having every next nearest neighbor pixel of the selected given pixel as a yellow pixel, which is described by the green storage bit as "1", the red bit as "0" and the blue bit as "1". The remaining nearest neighbor pixels around the given pixel are white with the red, green and blue storage bits all "1". Colors for the pixel blocks other than the unique colors are constructed in a similar fashion by mixing two preselected colors in the pixel blocks in the above described manner. This method of color construction further helps to reduce the cost of the apparatus 10 which substantially enhances the commercial significance and usefulness of the apparatus 10.

In the illustrated embodiment the color coding of the topographical map 44 is graphically explained to the user by generating alongside the map 44 a vertically positioned, color column or scale 46 having different color segments 48. The thirty-two colors in the illustrated embodiment are depicted by various cross hatching and line patterns. Each of the color segments 48 represents a fixed relative magnitude within a selected closed data set of the interpolated values 38 and 41 for the input activity signals 14. A closed data set is meant to include those input activity signals 14 measured on the patient's head 13 for a fixed set of measurement variables, such as, amplifier gain and the nature of the stimulus 16.

In alternative forms of the invention, the color scale 46 is positioned horizontally or is arranged alongside selected portions of any number of sides (for example, four if rectangular) of the topographical map 44. The user can also select the display of only the color segments 48 which are being displayed on the associated topographical map 44. This enables removal of unused colors to simplify association of colors with an amplitude at a selected location on the topographical maps 44.

In the illustrated embodiment of FIG. 5 in addition to the topographical map 44 and the color scale 46, the video display 43 also includes waveforms 50 which are characteristic of the EP response input activity signal 14 at the user selected electrode sensors 12. The user also can display the waveforms 50 associated with the interpolated values 38 and 41. Each of the waveforms 50 is output and displayed as a color coded line and also is identified using a conventional international format with an appropriate letter and number (for example, CZ, O1 and F7 in FIG. 5). The letter and number are indicative of the selected electrode sensor 12 or other interpolated point, such as one of the interpolated values 38 or 41.

In FIG. 5 are shown examples of the waveform 50 for EP response amplitudes which vary as a function of time above and below a centered zero base line. Typically, the EP response is measured over time periods of 256, 512, 1024 or 2048 milliseconds. The topographical maps 44 appear to the viewer as a series of frames showing the outline of the patient's head 13. Each of the frames is characteristic of the EP response amplitudes at a particular time after applying the stimulus 16 to the patient. For example, each frame can represent one particular four millisecond time segment of the total set of the frames which covers the time period from zero to 512 milliseconds in four millisecond increments. Therefore, for each of the user selected locations on the patient's head 13 for one of the frames, there is displayed the associated waveform 50. A particular point on the waveform 50 describes the amplitude for a particular time segment after the stimulus 16 has been applied to the patient. In order to pinpoint the time segment on the waveform 50, an indicator or a cursor 52 is displayed in FIG. 5 which points toward the time segment and to the amplitude on the waveform 50.

In the display of the topographical maps 44 of the EEG input activity signals 14 the user is able to select one of the locations (such as, at one of the sensors 12 or the interpolated values 38 or 41) on the patient's head 13 and generate adjacent the EEG topographical maps 44 an EEG curve of the contribution from the various frequency bands (i.e., α, β, δ and θ). The curve amplitude is correlated to an associated one of the frequency bands by using color coded segments positioned along the abscissa, or frequency, axis of the EEG curve. The color coded segment is indicative of preselected ones of the frequency bands, such as the α, β, δ and θ bands.

Figure 7:
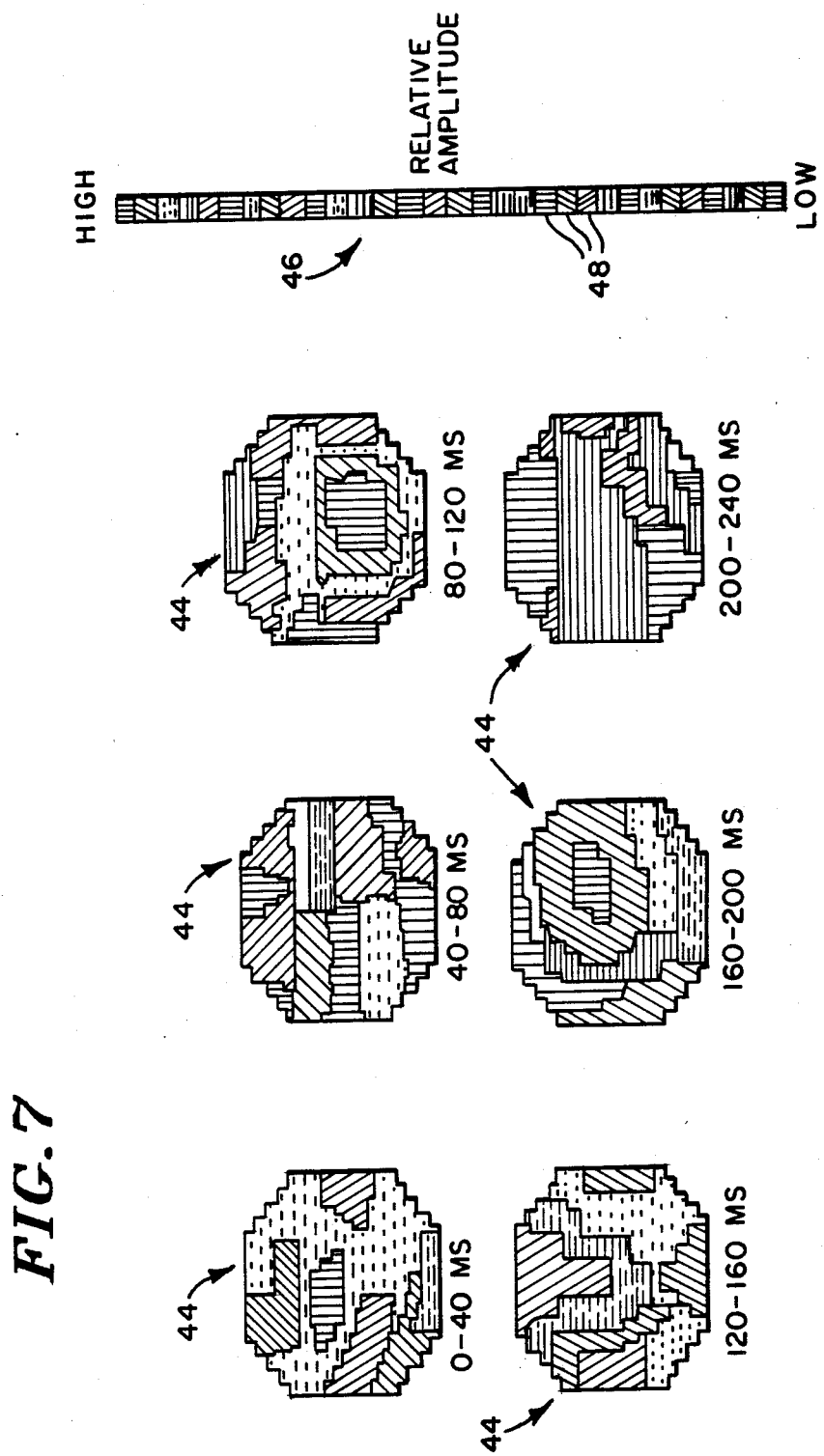
FIG. 7 is a display output of a plurality of topographical maps of evoked potential (EP) response measurements integrated over the time intervals shown.

The user of the apparatus 10 also has the ability to select the display of a plurality of reduced sizes of the topographical maps 44. This feature enables the user to display a number of the topographical maps 44 on a single screen of the video display 43 or a single page of a printed output. For example, in FIG. 7 is illustrated the display of a plurality of the topographical maps 44, along with the color scale 46. In alternative forms of the invention the user also displays the waveforms 50 for the same or for different locations in each of the plurality of the topographical maps 44. The user can also select to display different brain electrical activity states or different types of measurements for the reduced size topographical maps 44. For example, the user can select the display of EP responses and EEG information or EP responses characteristic of a plurality of different ones of the stimuli 16.

COMPUTER SOFTWARE

The apparatus 10 performs an analysis of the input activity signals 14 to provide the video output 37 responsive to various means, such as for example, computer means. In the illustrated embodiment of FIG. 1 the computer means comprises a computer software program selected by the user and the microprocessor unit 22 which executes the software program. In a preferred form of the invention shown in FIG. 1, the computer programs are stored on the disk or tape 29 and are loaded into the RAM 30 in preparation for execution by the microprocessor unit 22. In other forms of the invention, the computer programs of the computer means are input or downloaded from an external source, such as a remote software storage location (not shown) or a remote computer 53, into the RAM 30 in preparation for execution in the microprocessor unit 22. Alternatively, the computer programs are input directly into the microprocessor unit 22 for execution therein. The means for providing the video output 37 also can generally include any form of logic means, hardware and software, which performs an analysis responsive to computer software programs to analyze the amplified and digitized input activity signals 14 to generate the video output 37.

When the apparatus 10 processes data from a remote means, such as a remotely located polygraph or an electrode sensor 12 for sensing the signals 14, the signals 14 are input to an interface means (not shown). This interface means translates the signals 14 to enable communication by a modem over a telephone line or other suitable telecommunications equipment to the processing means and to logic or computer means for analysis to generate the video output 47. Such a form of the apparatus 10 avoids the need to have a dedicated system and makes feasible the measurement of the signals 14 at remote locations and enables the clinical use of the apparatus 10 by clinics and practioners who would otherwise be unable to support a dedicated system.

In the preferred embodiment, a master control program is provided as an executive which guides the user through the necessary steps for initial calibration of the apparatus 10, setting of apparatus parameters, including type of functions desired, topographical and Fourier transform data, filter characteristics, number of samples per second, display update frequency and so forth. The user calls up the executive program which then sequences the user through the appropriate command requests to provide for various functionality as described throughout this specification. The executive can be written in any plurality of languages, including assembly language, BASIC, FORTRAN, etc., and can operate under a plurality of commercially available operating systems, such as CP/M-86, MS-DOS or UNIX, on any of the plurality of commercial systems, such as the Zenith Z-100 system given as an example hereinbefore.

Once the apparatus 10 is calibrated and necessary set-up data is provided, the apparatus 10 can provide the topographical map 44 of the brain electrical activity in either live time, as sampled data is being acquired and stored, or mapping and display of the brain electrical activity can be performed on prestored or transferred data files not actually gathered in live time and can even be performed at an external, remote location relative to the apparatus 10. The mapping and display operation can be performed by the apparatus 10 and/or electronic hardware processing of the input activity signals 14. Hard copy printout on the printer 45 and/or output to the video display 43 can be provided at the user's selection.

In another form of the invention instead of the master control program, the apparatus 10 can provide all necessary functions by providing a plurality of separate callable software routines for the user to call up at his option. In this case, no central executive program would be required.

The software programs are utilized in certain selected modes of measurement and analysis, while other programs are utilized in all modes of measurement and analysis of brain electrical activity. These computer software programs are explained in the subsections described hereinbelow:

Digital Filtering

Figure 1B:
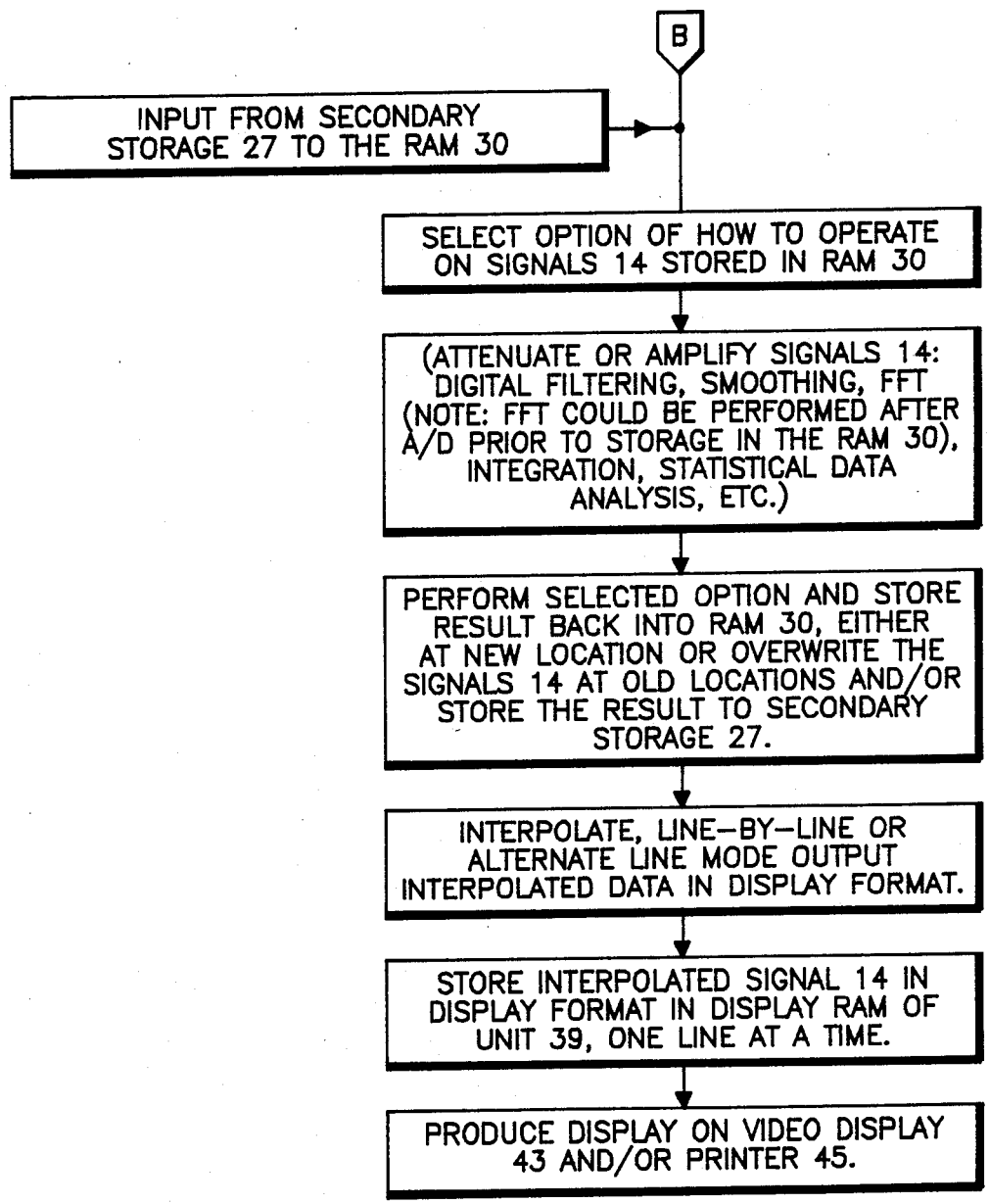

The digital filtering program is one form of an analyzer means which more particularly acts as a filter means, such as a digital filter 54 shown in FIG. 1. In selected areas of biological science the concept of digital filtering is a conventional method for removing or attenuating unwanted signals (see, for example, A. R. Moller, "Improving Brain Stem Auditory Evoked Potential Recordings by Digital Filtering," Ear and Hearing 2, 108–113 (1983); and A. V. Oppenheim et al., *Digital Signal Processing*, chap. 5, Prentice-Hall, Englewood Cliffs, N.J. 1975; which are incorporated by reference herein). In the present invention the user is able to attenuate or substantially remove unwanted extraneous signals from the input activity signals 14 by applying a digitized filter function thereto. The digitized filter function is loaded in the RAM 30 from the disk or tape 29 or from the remote computer 53. The digitized filter function is stored as attenuation (dB) in digitized form in the RAM 30 with an eight bit segment of the RAM 30 containing the attenuation value for one particular associated frequency. A complete frequency range for the digitized filter function is therefore embodied within a plurality of eight bit storage segments located in the RAM 30. More or less numbers of the segments can be utilized for more or less resolution of the frequency range. In performing the filtering operation the stored attenuation factors are applied to the stored amplitude at the associated frequencies to provide the reduced forms of the input activity signals 14.

In a conventional system a hardware based filter is usually applied before the signal 14 is digitized. Thus, the hardware filter is normally positioned immediately after the input activity signal 14 is output from the amplifier 26. However, in addition to attenuating unwanted signals, there is also some attenuation outside the optimum frequency range due to an inherent lack of a sharp cutoff in the attenuation for the hardware based filters. Further, the conventional hardware filter causes shifts in signal phase which distort the shape and position of the input activity signals 14. The digital filter 54 is however programmable to have a sharp cutoff and not introduce signal phase shifts when applied to the input activity signal 14. Nevertheless, where appropriate filter characteristics are achievable, the hardware filter could be utilized.

In the preferred form of the invention, the apparatus 10 uses the digital filter 54 derived from computer system hardware and software of the apparatus 10. Digital filtering is provided by the digital filter 54 responsive to the input activity signal 14 for locations after the accumulated averaged form of the signal 14 has been stored in the RAM 30, but before the interpolation has been performed. In other forms of the invention, the digital filter 54 is applied immediately after the input activity signal 14 is output from the multiplexer 24 (see FIG. 1) or after output from the A/D converter 28. Alternatively, the digital filter 54 is applied after the interpolated form of the input activity signal 14 has been generated.

In the illustrated embodiment, the digital filter 54 is applied after storage of the input activity signals 14 in the RAM 30. The original measured form of the input activity signal 14 is retained in unchanged form in the RAM 30; and therefore, the digital filter 54 can be changed and applied repeatedly to the input activity signal 14 in the process of the user analyzing the signal 14. The digital filter 54 is readily modified by user programming, and consequently the user has great versatility in constructing virtually any combination of low or high pass or band pass filter necessary to analyze the input activity signal 14.

Noise Evaluation

The evaluation of a noise signal often enables the user to compensate for the noise by utilizing an electronic filter, such as the digital filter 54, to attenuate the noise signal to provide a reduced, or substantially noise-free, form of the input activity signal 14 for more meaningful data analysis. Alternatively, if the user can identify the source of the noise signal, the noise source might be eliminated altogether. Noise identification and attenuation or reduction is known in selected areas of biological science (see, for example, *Introduction to Automated Arrhythmia Detection*, ch.5, K. L. Ripley and A. Murray, IEEE Computer Society, No. EH 0171.9,1980; and see R. H. Wong and R. G. Bickford, "Brainstem Auditory Evoked Potentials: The Use of Noise Estimates," Electroencephelography 50, 35-34, (1980); which are incorporated by reference herein).

Another aspect of the analyzer means is noise evaluation alone which is carried out by the apparatus 10 responsive to software programs directed to determination of the noise signals. Knowing the noise signal behavior, the user can often program the digital filter 54 to attenuate the noise signal. One type of noise evaluation program is directed to evaluation of noise signals which do not have long term, constant frequency and amplitude. This type of noise evaluation is directed to, for example, noise signals comprising random noise, spurious occasional components of irregular frequency and varying amplitude and spurious temporary components of regular frequency noise.

Figure 6:
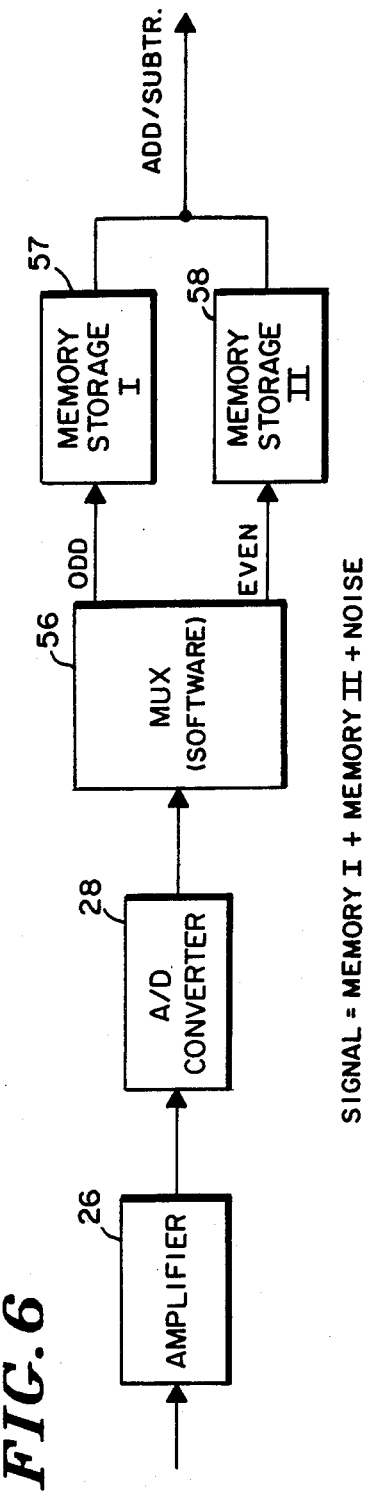
FIG. 6 is a block diagram of a noise signal evaluation procedure.

FIG. 6 illustrates one embodiment of the invention used for isolation of extraneous noise signals present in the measurement of brain electrical activity signals. The converted input activity signal 14 output from the A/D converter 28 is input to multiplexer means, such as a multiplexer 56, which distributes and accumulates the activity signal 14 in at least two alternate memory locations, a first memory 57 and a second memory 58. The signal 14 is entered into these locations by alternating data entry between the memory locations 57 and 58. If the noise signal is random noise or is a continuous but irregular frequency signal, the noise signal is characterizable by applying subtraction means to generate a subtracted output of the arithmetic difference between the input activity signals 14 in the first memory location 57 and the input activity signals 14 in the second memory location 58. Knowing the noise signal, the user can selectively attenuate this unwanted noise signal using filters, such as the digital filter 54. If, however, the noise signal happens to be similar in frequency to the input activity signal 14, the filtration is more difficult. In such cases the user might have to eliminate the source of the noise signal or alter experimental conditions to distinguish and attenuate the noise signal.

The nature of the noise signal to be evaluated also affects the analysis procedure, such as the number of values of the signal 14 to be entered in each of the memory locations 57 or 58 before switching data entry to the other memory location 57 or 58. For evaluating random noise signals, it is acceptable to enter every odd numbered data signal in the first memory location 57 and every even numbered data signal in the second memory location 58. For example, when measuring EP response curves, every other set of values which constitute the EP response to the stimulus 16 is accumulated in the first memory location 57 and the other sets of responses are accumulated in the location 58.

When the noise spectrum takes other forms, such as a spurious noise burst of irregular frequency and amplitude, correct analysis of the noise signal depends on having a substantial portion of the noise signal isolated within one segment (or other identifiable portion) of one of the memory locations 57 or 58. If the noise signal is evenly distributed in the memory locations 56 and 58, this method does not enable one to readily distinguish the noise signal portion. Therefore, in general, data is stored and accumulated in one of a plurality of memory locations with a user selectable time period for accumulating data in each of the memory locations before switching to another of the memory locations. For example, ten entries of the signal 14 can be stored in one of a plurality of memory locations before switching to the next memory location for the next ten entries of the signal 14. Accordingly, the user should determine by independent analysis the expected varieties of noise and select the number of data entries and time period for accumulation in each of the memory locations. In this manner, noise signals which have a particular time duration can be isolated. After determination of the noise signal and of the noise corrected form of the input activity signal 14, the user can also evaluate the noise signal by calculation of a signal to noise ratio which assists in evaluating the nature and magnitude of the noise signal and provides a way to evaluate the quality of the experimental conditions.

In another form of the invention the apparatus 10 responsive to analyzer means in the form of a software program evaluates the noise signal by performing a Fourier transformation to isolate the frequency components associated with the noise signal. The Fourier transformation is preferably carried out as a fast Fourier transformation procedure in a conventional manner as indicated hereinafter. Once the noise signal has been evaluated, the digital filter 54 is programmed to attenuate the known noise signal. This Fourier transformation analysis can also be preceded or followed by one of the previously discussed procedures for analyzing the noise signals.

Statistical Analysis

Statistical evaluation of an individual patient's characteristic topographical map of brain electrical activity is accomplished by such conventional approaches as z-statistics and t-statistics (see, for example, U.S. Pat. Nos. 4,201,224 (John) and 3,780,724 (John) which are incorporated by reference herein). For example, in the case of z-statistics, the patient response in terms of the input activity signals 14 at each of the points of the topographical map 44 is expressed in terms of the number of standard deviations from the average response of a group of a representative normal population.

Fourier Transformation

The apparatus 10 responsive to a software program carries out a Fourier transformation analysis of the frequency energy components in an EEG measurement. As mentioned hereinbefore, a conventional fast Fourier transformation (FFT) is preferably used to carry out the transformation of the signals 14. The FFT is explained by Oppenheim et al., *Digital Signal Processing*, ch. 6, Prentice-Hall, Englewood Cliffs, N.J., 1975, which is incorporated by reference herein.

The EEG input activity signals 14 are sampled at predetermined time intervals, approximately 2.5 second segments, to provide a selectable total number of 256 to 2048 segments of the sampled form of the EEG input activity signals 14 (see, for example, Ueno et al., "Topographic Computer Display of Abnormal EEG Activities in Patients with CNS Diseases," Memoirs of the Faculty of Engineering, Kyushu University, Volume 34, February, 1975, pages 195-209; which is incorporated by reference herein). In the illustrated embodiment sampling means for obtaining the signal samples takes the form of a software program in the disk 29 and is executed by the microprocessor unit 22. The software program actuates measurement of the signals 14 at the predetermined time intervals in accordance with a timing routine. The output from the Fourier transformation analysis of the segments of the input activity signal 14 enables determination of the frequency band energy output present in at least the major EEG frequency bands of $\alpha$, $\beta$, $\delta$ and $\theta$. In another form of the invention other subintervals of some of these bands are also evaluated. The frequency band energy outputs can be further analyzed by one of the statistical analysis software programs and/or the noise evaluation programs. The frequency band energy outputs are then processed by the DPU 39, and the video display 43 generates the appropriate topographical map 44.

Threshold Activation

In some modes of data acquisition, it is desirable not to enable, or actuate, accumulation and analysis of data unless the incoming input activity signals 14 attain or exceed a predetermined condition, such as a predetermined threshold amplitude or frequency level. This approach allows particular classes of data to be analyzed without superfluous data being present. For example, epileptic spikes occur intermittently and generate a large amplitude spike.

After a preliminary screening of the patient, threshold activation program data in the form of the predetermined condition is established and is placed by the input means (such as the keyboard 23 or the disk 29) into the RAM 30 or into separate hardware means for storing and testing the predetermined condition such as threshold test circuitry 55 shown in FIG. 1. The microprocessor unit 22 uses the predetermined condition stored in the RAM 30, or embodied within the circuitry 55, to compare with the incoming input activity signals 14. Therefore, the input activity signals 14 are stored and analyzed by the apparatus 10 only if the signal amplitude exceeds the predetermined condition.

In an alternative form of the invention the apparatus 10, responsive to a software program, carries out a differentiation of the incoming input activity signal 14, and when the amplitude of the differentiated signal exceeds the predetermined condition, the apparatus 10 accumulates and analyzes the signal 14. In this manner the onset of a sharp spike, such as an epileptic spike having a rapidly changing curve slope, is detected, and the spike subsequently undergoes analysis.

In another form of the invention the apparatus 10, responsive to the threshold activation program data, detects and analyzes a predetermined threshold frequency level by employing frequency means in the form of conventional frequency counting circuitry (see, for example, "Electronics for Scientists and Engineers", Prentice Hall, Englewood Cliffs, N.J., 1967, pages 321-322 and 470-473, which is incorporated by reference herein). The output from the frequency counting circuit is a signal whose amplitude is proportional to the frequency detected; therefore, the predetermined condition for the threshold frequency level is set to actuate data acquisition and analysis of the incoming input activity signal 14 whenever the predetermined frequency level has been exceeded.

In another aspect of the invention the apparatus 10 measures the number of zero crossing events (a form of frequency determination) and data taking is activated upon exceeding a predetermined number of such events. The microprocessor unit 22 or the test circuitry 55 evaluates the algebraic sign for each one of the input activity signals 14 and maintains a running count of the number of changes in the algebraic sign within a given time period. When the number of algebraic sign changes within the given time period exceeds a predetermined number, data accumulation and analysis is activated, and the resulting input activity signals 14 are displayed as the topographical maps 44.

The apparatus 10 responsive to the threshold activation program is able to actuate analysis of any of the input activity signals 14 wherein the user wishes to restrict analysis, for examle, to a large amplitude signal, to a high frequency signal or to other selected distinguishable features Advantages of the threshold activation program include use of less overall storage area in memory for analysis of the signals 14, performance of more detailed data analysis in a given time period of actual calculation by the microprocessor and faster and more efficient analysis of a complete data set compared to the case of analyzing all incoming data.

Integration, Differentiation and Difference Measurements

The apparatus 10 responsive to an integration software program operates on frames of the input activity signals 14 measured for EP responses to characterize the time integrated response output. This integrated output enables an evaluation of spatial locations on the patient's head 13 and/or the time segments of the EP response which make the most important contributions to the input activity signals 14. Integration is carried out over a range of user selected time segments, and in FIG. 7 the integrated output for some of the selectable time segments is displayed in the resulting topographical maps 44. The integrated output of the input activity signals 14 of the topographical maps 44 results in combining a number of separate smaller time period segments of the input activity signals 14. Therefore, the user views in a small number of the topographical maps 44 the behavior of the input activity signals 14 over a broad time range. The time range of 0 to 240 milliseconds is shown in only six frames of integrated EP response. Such a display mode is therefore beneficial to the user to carry on an evaluation of a large amount of data without requiring separate display of a large number of the topographical maps 44 and without having to switch between a large number of the topographical maps 44.

The apparatus 10 responsive to a differentiation software program operates on frames of the input activity signals 14 from EP responses to characterize the first or second order differential of the EP responses. This differential response enables an evaluation of locations of the time segments which contain the most significant contributions to changes (first order) and rate of change (second order) in the amplitude with respect to location and time of the EP response curves. The user can select the spatial location and/or the time interval over which the differentiation is calculated. The analysis enables spatial and time analysis of rapidly changing EP responses which supplements information obtained from the integration output. The analysis can also be carried out for changes and rate of change in amplitude with respect to location for the EEG input activity signals 14.

The apparatus 10 is also responsive to a difference software program which operates on frames of the input activity signals 14 from the EP responses to evaluate the arithmetic difference from one of the user selected frames to another, each of the frames characteristic of a preselected time after application of the stimulus 16.

Montage Analysis

The apparatus 10 responsive to a computer montage analysis program carries out a difference type of analysis of the input activity signals 14 to isolate and identify features of interest, such as epileptic spikes. The analysis is accomplished by selecting one or more of the electrode sensors 12 as reference electrodes with the rest of the electrode sensors 12 having the role of active electrode sensors 12. The montage analysis is performed by using the input activity signals 14 stored in memory means, such as the RAM 30, and thus repeated actual measurements are unnecessary. In a preferred form of the invention the twenty-one electrode sensors in FIG. 1 are assigned active roles and an additional electrode sensor 12 is attached near the patient's ear to act as the reference electrode sensor 12. The difference form of the input activity signal 14 is calculated, and the values are stored in the RAM 30. The user then views the difference signals 14 and determines the approximate location of the feature of interest. The user next selects a new one of the reference electrode sensor 12 and active electrode sensors 12 which are in close proximity to the feature of interest. The difference form of the input activity signals 14 are calculated, and the location and appearance of the feature of interest is isolated with greater precision. This iteration continues by recycling back to the selection of new ones of the reference and active electrode sensors 12 until completion of the identification of the feature of interest In other forms of the invention for each selected set of the reference and active electrode sensors 12, an average value can be calculated for each set of the sensors 12 in every frame of the input activity signals 14. These average values are then subtracted from one another to form the difference form of the signals 14. For example, if the feature of interest is a sharp peak extending along a line, the user could select ten of the sensors on one side of the distended peak as reference electrodes and eleven on the other side as active electrodes. The average of each set is then subtracted from the average of the other for each of the frames. The difference form of the input activity signals 14 is then calculated for a selected number of the frames, (for example, the user can select from the 240 frames for measurements of the EP response taken every four milliseconds from 0 to 960 milliseconds after the application of the stimulus 16). As discussed hereinabove, this iterative analysis procedure can be repeated using recycle means to return to the beginning of the montage iterative analysis procedure by selecting a different set of the electrode sensors 12 as the reference electrode sensor 12. This iterative process is continued until the source of any feature of interest, such as the above mentioned distended type of peak, is identified or isolated. This procedure can be programmed to iterate automatically to a solution, or the user can interact to select various combinations of active and reference electrode sensors 12 to locate the most prominent features. Therefore, the recycle means can be a user signal to return to perform another iterative analysis or can be an interrupt and branching command in the software program to automatically recycle until the specified feature is identified in accordance with predetermined conditions stored in the RAM 30. The resulting set of difference input activity signals are stored in the RAM 30 at locations different from the input activity signals 14 and are compared to one another. These difference input activity signals 14 can also undergo the additional analysis 40 and provide other forms of the topographical maps 44 of EP response and EEG measurements. Display of the difference signals 14 and their derivatives from the analysis 40 enable diagnosis of disparities associated with brain abnormalities.

Montage analysis has important advantages over the prior art because the instant approach uses only one set of the measured input activity signals 14 which are stored in the RAM 30. Conventional methods, however, require repeated measurements since the montage analysis proceeds by selecting a first set of one or more reference electrode sensors 12, measuring a set of signals for the remainder of the plurality of the electrode sensors 12, computing and recording the difference of the signals 14, establishing a new set of reference electrode sensors 12 and measuring a new set of differences in the signals 14. This procedure is sequentially repeated until the location of the feature of interest has been isolated. The computer program montage analysis renders unnecessary this time consuming and repetitive task and substantially reduces the time for data taking and analysis.

Cognitive Test Mode

The apparatus 10 responsive to a cognitive testing software program effectuates tests of recognition ability which enables diagnosis of a number of abnormalities (see, for example, U.S. Pat. No. 3,901,215 (John) which is incorporated by reference herein). The instant cognitive testing program makes full use of a period of data acquisition by sorting the responses to different types of the stimuli 16 into different memory locations of the RAM 30. Ordinarily cognitive testing is accomplished by acquiring the input activity signals 14 for a plurality of completely different time periods, wherein each time period is devoted solely to either a regular form of the stimulus 16 and response thereto or to an intermittent form of the stimulus 16 and associated response. Examples of the different types of the stimuli 16 can include a mixture of different amplitude audible tones, tones of different frequency and a tone pattern with intermittent absences of certain anticipated tones.

The microprocessor unit 22 controls administration of the predetermined pattern of the stimulus 16 during the cognitive testing mode of operation responsive to the cognitive test software, and therefore the microprocessor unit 22 flags each of the applied stimuli 16. Epending on the nature of the stimulus 16 the flagging enables the microprocessor 22 to sort the resulting EP responses comprised of a set of the input activity signals 14 associated with each type of the stimulus 16, into the different memory locations. Comparison and analysis, such as statistical analysis, is then performed on the signals 14 stored in the different memory locations. This procedure therefore makes data collection more efficient and reduces the time to collect sufficient data characteristic of the input activity signals 14.

Video Display and Interaction Modes

The apparatus 10 responsive to an interlace software program results in the interpolation and the output to the display memory of the DPU 39 of every other pixel line in one frame to the video display 43. Upon completion of display of every other pixel line in a first complete frame or first topographical map 44, the program causes return of the raster beam to the beginning of the display cycle to perform alternate pixel line interpolation and display in the next frame, or the next topographical map 44, of the set of pixel lines skipped in the first display cycle. By virtue of having to process and display only every other pixel line of the input activity signals 14, the interlace mode enables an apparent increase in display speed by updating at, for example, twelve frames/second the display memory of the DPU 39. The video display 43 therefore generates a plurality of the topographical maps 44 at an apparent rate of nearly twenty-four frames/second because in each frame every other pixel line is displayed. This results in a smooth cartooning effect without apparent loss of resolution to the human eye.

In the interaction modes the mouse 36 or the light pen 34 are preferably used as indicator means. The user generates an input signal so as to interact with the information present on the video display 43 thereby actuating selected software programs. In the case of the mouse 34, this use takes the form of displaying a variety of selectable routines on the video display 43, moving a cursor to point to a designated label for one of the routines and carrying out the routine by actuating a switch (not shown) on the mouse 36. Similarly, for the light pen 34, the user points to a location on the video display 43, and a screen sensor (not shown) detects the site of the light pen light spot and generates an activation output to the microprocessor unit 22 to actuate the appropriate software program. The software program also displays additional information relevant to the displayed topographic map 44, or further calculations can be performed and displayed. For example, the user is able to selectively display the evoked potential waveforms 50 (illustrated in FIG. 5) for those points on the topographic map 44 designated by the mouse 34 or by the light pen 34.

In another form of the invention, the apparatus 10 responsive to an interaction means in the form of a software program can generate the amplitude of input activity signal contours along any indicated line on the topographical map 44, the line being selected by the cursor of the mouse 36 or by the light pen 34. Further, the software program can act as a map magnifying means by allowing the user to utilize the mouse 36 or the light pen 34 to select an outline of an area of the topographical map 44 and expand the delineated portion to fill a selected portion of the video display 43.

While preferred embodiments of the present invention have been illustrated and described, it will be understood that changes and modifications can be made without departing from the invention in the broader aspects. Various features of the invention are set forth in the following claims.

What is claimed is:

1. An apparatus for displaying a topographical map of brain electrical acitivity of a patient, comprising:
    sensor means disposed on a patient's head for providing changeable amplitude sign input activity signals responsive to said brain electrical activity;
    processing means responsive to said changeable amplitude sign input activity signals for providing an amplified and digitized form of said input activity signals;
    means for providing a video output responsive to said amplified and digitized input activity signals, said video output incluidng a set of interpolated input activity signals for positions between the locations of said sensor means with said positions including selected locations along at least two interpolated lines generated between adjacent pairs of lines formed by connecting the locations of said sensor means and at least two of said interpolated lines between each said adjacent pairs of lines being generated from distinguishable appropriate combinations of said input activity signals, said interpolated input activity signals generated line—by—line and displayed while a next successive adjacent line for display is being generated; and
    means for displaying said topographical map of said brain electrical activity responsive to said video output.

2. The apparatus as defined in claim 1 wherein said sensor means comprises a plurality of electrode sensors.

3. The apparatus as defined in claim 1 wherein said set of interpolated input activity signals are generated from linear weighted appropriate pairs of said amplified and digitized input activity signals.

4. The apparatus as defined in claim 1 further comprising means for providing statistically averaged values for said input activity signals responsive to said amplified and digitized input activity signals.

5. The apparatus as defined in claim 4 wherein said means for providing averaged values comprises a computer having a random access memory.

6. The apparatus as defined in claim 1 further including color code means for displaying alongside said topographical maps a predetermined set of colors displayable on said topographical maps, each of said colors representing an associated fixed relative value within a selected closed data set of said input activity signals.

7. The apparatus as defined in claim 6 wherein said color code means alongside each said topographical map includes at least said colors being displayed on each said topographical map associated with said color code means.

8. The apparatus as defined in claim 1 wherein said means for displaying includes a display processing unit having a display memory which is updated for display of selected ones of said lines of said topographical maps responsive to said input activity signal.

9. The apparatus as defined in claim 1 wherein said topographic maps are constructed from pixels having a plurality of distinguishable colors, wherein each of said colors is selectively comprised of one unique color and of at least two unique colors mixed in a predetermined manner among near neighbors of said pixels.

10. An apparatus for displaying a topographical map of brain electrical activity sensed by a plurality of electrode sensors disposed on a patient's head, wherein said electrode sensors provide an associated plurality of input activity signals, said apparatus comprising:
   processing means for providing an amplified and digitized form of said plurality of input activity signals;
   computer means for providing a video output responsive to said plurality of amplified and digitized input activity signals, said video output including a set of interpolated input activity signals for positions between the locations of said electrode sensors with said positions including selected locations along at least two interpolated lines generated between adjacent pairs of lines formed by connecting the locations of said electrode sensors and at least two of said interpolated lines between each said adjacent pairs of lines being generated from distinguishable appropriate combinations of said input activity signals;
   means for displaying said topographical maps of said brain electrical activity responsive to said video output; and
   color code means for displaying near each of said topographical maps a predetermined set of colors displayable on an associated one of said topographical maps, each of said colors representing an associated fixed relative value within a selected closed data set of said input activity signals.

11. The apparatus as in claim 10 further characterized in that said interpolated input activity signals have changeable amplitude sign and are generated line—by—line, wherein display of each line is provided while a next successive adjacent line for display is being generated.

12. The apparatus as defined in claim 10 wherein said predetermined set of colors is positionable along a portion of said topographical map.

13. The apparatus as defined in claim 10 wherein said predetermined set of colors is positionable on the display along at least one of a vertical scale and a horizontal scale.

14. The apparatus as defined in claim 10 further including indicator means responsive to a user input for supplying an input signal for actuating selected software programs to control said video output on said display means.

15. The apparatus as defined in claim 14 further comprising map magnifying means responsive to said input signal for selectively enlarging a predetermined portion of said topographical map for display.

16. An apparatus for displaying a plurality of topographical maps of brain electrical activity sensed by a plurality of electrode sensors disposed on a patient's head, wherein said sensors provide an associated plurality of changeable amplitude sign input activity signals responsive to said brain electrical activity, said apparatus comprising:
   processing means connected to be responsive to said changeable amplitude sign input activity signal for providing an amplified and digitized form of said input activity signals;
   means for providing a video output responsive to said amplified and digitized input activity signals, said video output including a set of interpolated input activity signals for positions between the locations of said plurality of sensors with said positions including selected locations along at least two interpolated lines generated between adjacent pairs of lines formed by connecting the locations of said sensors and at least two of said interpolated lines between each said adjacent pairs of lines being generated from distinguishable appropriate combinations of said input activity signals and said interpolated input activity signals are generated and displayed line—by—line while a next successive adjacent line for display is being generated by said means for providing a video output; and
   means for displaying simultaneously a display of a plurality of said topographical maps of said brain electrical activity responsive to said video output.

17. The apparatus as defined in claim 16 wherein said plurality of topographical maps comprises a plurality of different selectable states of said brain electrical activity.

18. The apparatus as defined in claim 17 wherein said different selectable states comprise an evoked potential response, an integrated time segment of evoked potential response and a Fourier transform of EEG input activity signals.

19. An apparatus for displaying topographical maps of brain electrical activity of a patient's head comprising:
   a plurality of electrode sensors disposed on said patient's head, said sensors providing an associated plurality of changeable amplitude sign input activity signals in response to said brain electrical activity;
   processing means connected to be responsive to said input activity signals for providing an amplified and digitized form of said changeable amplitude sign input activity signals;
   means for providing a video output responsive to said plurality of amplified and digitized input activity signals, said video output including a set of interpolated input activity signals for positions between the locations of said plurality of sensors with said positions including selected locations along at least two interpolated lines generated between adjacent pairs of lines formed by connecting the locations of said sensors and at least two of said interpolated lines between each said adjacent pairs of lines being generated from distinguishable appropriate combinations of said input activity signals;
   input means for supplying an input signal responsive to a user input, said input means controlling the information characterized by said video output: and
   means for displaying said topographical maps of said brain electrical activity responsive to said video output, said display means including display processing means having a display memory which can be updated for display of user selected lines of said topographical maps responsive to said input activity signal.

20. The apparatus as defined in claim 19 wherein said means for providing a video output comprises logic means responsive to computer software programs for providing said video output responsive to said amplified and digitized input activity signals.

21. The apparatus as defined in claim 19 further including color code means for displaying near each of said topographical maps at least a portion of a predetermined set of colors, each of said colors appearing on an associated one of said topographical maps and each of said colors having an associated fixed relative value within a selected closed data set of said input activity signals.

22. The apparatus as defined in claim 21 wherein said predetermined set of colors is arrangeable for display alongside a portion of said topographical map.

23. The apparatus as defined in claim 21 wherein said predetermined set of colors is arrangeable for display along at least one of a vertical scale and a horizontal scale.

24. The apparatus as defined in claim 19 further characterized in that said display includes at least one evoked potential response waveform plotted near each of said topographical maps, each said waveform characteristic of an amplitude and time response for a selected location on said topographical map.

25. An apparatus for displaying a topographical map of EEG brain electrical activity in a plurality of frequency bands of a patient, comprising:

a plurality of electrode sensors disposed on a patient's head for measuring EEG input activity signals at each of said plurality of electrode sensors;

processing means connected to be responsive to said input activity signals for providing an amplified and digitized form of said input activity signals;

means for sampling said amplified and digitized form of said EEG inout activity signals at predetermined intervals responsive to said amplified and digitized form of said input activity signals to provide sampled forms of said EEG input activity signals;

means for performing a Fourier transform of said sampled forms of EEG input activity signals responsive thereto to provide a frequency band energy output characteristic of the energy in each of said plurality of frequency bands;

computer means responsive to said frequency band energy output for generating a set of interpolated frequency band energy output signals for positions between the locations of said plurality of sensors, said output signals generated for said positions including selected locations along at least two interpolated lines generated between adjacent pairs of lines formed by connecting the locations of said sensors and at least two of said interpolated lines between each said adjacent pairs of lines being generated from distinguishable appropriate combinations of said input activity signals; and display means for displaying said topographical map responsive to said frequency band energy output signals.

26. The apparatus as defined in claim 25 further including a display of at least one EEG curve plotted near each said topographical map, each said EEG curve characteristic of the amplitude within each said frequency band.

27. The apparatus as defined in claim 26 wherein said display of EEG curves can be color coded by positioning selected color coded segments along the frequency axis of said EEG curve, each of said color coded segments associated with a preselected one of said frequency bands.

28. An apparatus for displaying a topographical map of brain electrical activity sensed by a plurality of electrode sensors disposed on a patient's head, wherein said electrode sensors provide an associated plurality of input activity signals, said apparatus comprising:

processing means for providing an amplified and digitized form of said plurality of input activity signals;

computer means for providing a video output responsive to said plurality of amplified and digitized input activity signals;

means for displaying said topographical maps of said brain electrical activity responsive to said video output; and input means for supplying an input signal responsive to a user input and indicator means connected to be responsive to said input signal for actuating selected software programs to control said video output on said means for displaying, said indicator means able to select a line on said topographical map and actuate said computer means to display amplitudes of said input activity signals along said line.

* * * * *